(12) United States Patent
Thakur et al.

(10) Patent No.: US 11,172,832 B2
(45) Date of Patent: Nov. 16, 2021

(54) SYSTEMS AND METHODS FOR EVALUATING HEMODYNAMIC RESPONSE TO ATRIAL FIBRILLATION

(71) Applicant: Cardiac Pacemakers, Inc., St. Paul, MN (US)

(72) Inventors: Pramodsingh Hirasingh Thakur, Woodbury, MN (US); Ramesh Wariar, Blaine, MN (US); Qi An, Blaine, MN (US); Barun Maskara, Blaine, MN (US); Yi Zhang, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 603 days.

(21) Appl. No.: 14/723,004

(22) Filed: May 27, 2015

(65) Prior Publication Data

US 2015/0342487 A1  Dec. 3, 2015

Related U.S. Application Data

(60) Provisional application No. 62/006,595, filed on Jun. 2, 2014.

(51) Int. Cl.
*A61B 5/0205* (2006.01)
*A61B 5/08* (2006.01)
(Continued)

(52) U.S. Cl.
CPC ............ *A61B 5/0205* (2013.01); *A61B 5/026* (2013.01); *A61B 5/0245* (2013.01);
(Continued)

(58) Field of Classification Search
USPC ........................................................ 600/484
See application file for complete search history.

(56) References Cited

U.S. PATENT DOCUMENTS 6,491,639 B1   12/2002  Turcott
7,194,306 B1    3/2007  Turcott
(Continued)

FOREIGN PATENT DOCUMENTS

CN    106456003 A    2/2017
GB      2428977 A    2/2007
(Continued)

OTHER PUBLICATIONS

Naqvi, Tasneem Z., et al., "Method of Atrioventricular Programming in Atrial Flutter in Patients with Biventricular Pacemaker", PACE, vol. 30, (Aug. 2007), 948-956.
(Continued)

*Primary Examiner* — Christian Jang
*Assistant Examiner* — Mitchell E Alter
(74) *Attorney, Agent, or Firm* — Schwegman Lundberg & Woessner, P.A.

(57) ABSTRACT

Systems and methods for assessing hemodynamic status of a patient experiencing atrial tachyarrhythmia such as an atrial fibrillation (AF) episode are disclosed. A system can comprise an atrial tachyarrhythmia detection circuit configured to detect an AF episode, a hemodynamic sensor circuit configured to sense at least one hemodynamic signal, and a hemodynamic status analyzer circuit that can calculate one or more signal metrics using the sensed hemodynamic signal during the AF episode. The hemodynamic status analyzer circuit can categorize the hemodynamic status of the patient into one of two or more categorical hemodynamic status levels which indicate elevated hemodynamic impact of the detected AF episode. A user interface can provide to an end-user a presentation of the categorized hemodynamic status level during AF.

17 Claims, 6 Drawing Sheets

(51) Int. Cl.

| | | |
|---|---|---|
| *A61B 7/04* | (2006.01) | |
| *A61B 5/0245* | (2006.01) | |
| *A61B 5/0537* | (2021.01) | |
| *A61B 5/00* | (2006.01) | |
| *A61B 5/11* | (2006.01) | |
| *A61B 5/026* | (2006.01) | |
| *A61B 5/024* | (2006.01) | |
| *A61N 1/365* | (2006.01) | |
| *A61N 1/39* | (2006.01) | |
| *G16H 50/30* | (2018.01) | |
| *G16H 50/20* | (2018.01) | |
| *A61B 5/361* | (2021.01) | |
| *A61B 5/363* | (2021.01) | |
| *A61B 5/0215* | (2006.01) | |
| *A61B 5/145* | (2006.01) | |

(52) U.S. Cl.
CPC ........ *A61B 5/02405* (2013.01); *A61B 5/0537* (2013.01); *A61B 5/08* (2013.01); *A61B 5/0809* (2013.01); *A61B 5/0816* (2013.01); *A61B 5/1107* (2013.01); *A61B 5/361* (2021.01); *A61B 5/363* (2021.01); *A61B 5/7264* (2013.01); *A61B 5/7275* (2013.01); *A61B 7/04* (2013.01); *A61N 1/36585* (2013.01); *A61N 1/395* (2013.01); *A61N 1/3987* (2013.01); *G16H 50/20* (2018.01); *G16H 50/30* (2018.01); *A61B 5/0022* (2013.01); *A61B 5/0215* (2013.01); *A61B 5/02055* (2013.01); *A61B 5/02438* (2013.01); *A61B 5/0826* (2013.01); *A61B 5/1118* (2013.01); *A61B 5/14542* (2013.01); *A61N 1/36521* (2013.01); *A61N 1/36578* (2013.01)

(56) References Cited

U.S. PATENT DOCUMENTS

| | | | |
|---|---|---|---|
| 7,336,994 B2 | 2/2008 | Hettrick et al. | |
| 7,890,162 B2 | 2/2011 | Cho | |
| 7,925,348 B1 | 4/2011 | Bornzin et al. | |
| 8,626,278 B2 | 1/2014 | Parks et al. | |
| 2006/0069322 A1 | 3/2006 | Zhang et al. | |
| 2006/0095083 A1 | 5/2006 | Zhang et al. | |
| 2006/0106322 A1* | 5/2006 | Arand | A61B 5/0402 600/514 |
| 2006/0116593 A1 | 6/2006 | Zhang et al. | |
| 2006/0253043 A1 | 11/2006 | Zhang et al. | |
| 2006/0253044 A1 | 11/2006 | Zhang | |
| 2006/0253162 A1 | 11/2006 | Zhang et al. | |
| 2006/0253164 A1 | 11/2006 | Zhang et al. | |
| 2007/0142733 A1* | 6/2007 | Hatlestad | A61B 5/0535 600/508 |
| 2007/0149890 A1 | 6/2007 | Li et al. | |
| 2007/0167849 A1 | 7/2007 | Zhang et al. | |
| 2009/0076557 A1 | 3/2009 | Zhang et al. | |
| 2009/0131996 A1* | 5/2009 | Li | A61N 1/36514 607/4 |
| 2010/0023078 A1 | 1/2010 | Dong et al. | |
| 2010/0198285 A1 | 8/2010 | Rom | |
| 2010/0274146 A1* | 10/2010 | Li | A61N 1/3962 600/515 |
| 2010/0280841 A1* | 11/2010 | Dong | A61B 5/04012 705/2 |
| 2010/0298729 A1 | 11/2010 | Zhang et al. | |
| 2011/0137192 A1 | 6/2011 | Zhang et al. | |
| 2011/0144511 A1 | 6/2011 | Zhang et al. | |
| 2011/0196439 A1 | 8/2011 | Li et al. | |
| 2011/0224555 A1 | 9/2011 | Park | |
| 2012/0221066 A1 | 8/2012 | Rosenberg et al. | |
| 2012/0221069 A1 | 8/2012 | Rosenberg et al. | |
| 2012/0226328 A1 | 9/2012 | Dong et al. | |
| 2012/0245475 A1 | 9/2012 | Hatlestad et al. | |
| 2012/0289847 A1 | 11/2012 | Zhang et al. | |
| 2012/0330171 A1 | 12/2012 | Zhang et al. | |
| 2013/0165802 A1 | 6/2013 | Dalal et al. | |
| 2013/0184545 A1 | 7/2013 | Blomqvist et al. | |
| 2013/0204312 A1 | 8/2013 | Gill et al. | |
| 2013/0325083 A1 | 12/2013 | Bharmi | |

FOREIGN PATENT DOCUMENTS

| | | |
|---|---|---|
| WO | WO 2011/084636 A2 * | 7/2011 |
| WO | WO-2012099534 A2 | 7/2012 |
| WO | WO-2015187424 A1 | 12/2015 |

OTHER PUBLICATIONS

Waggoner, Alan D., et al., "Improvements in Left Ventricular Diastolic Function After Cardiac Resynchronization Therapy Are Coupled to Response in Systolic Performance", JAAC; vol. 46, No. 12, (Dec. 20, 2005), 2244-2249.

"International Application Serial No. PCT/US2015/032649, International Preliminary Report on Patentability dated Dec. 15, 2016", 8 pgs.

"International Application Serial No. PCT/US2015/032649, International Search Report dated Sep. 30, 2015", 4 pgs.

"International Application Serial No. PCT/US2015/032649, Written Opinion dated Sep. 30, 2015", 7 pgs.

Muna, Hassan Hammash, et al., "Cardiac rhythm during mechanical ventilation and weaning from ventilation", XP055215840, ISBN: 978-1-26-709380-6, Retrieved from the Internet: <RL:http://search.proquest.com/docvi ew/915 016893>, (Jun. 24, 2010), 24-30.

"Chinese Application Serial No. 201580030239.6, Office Action dated Dec. 28, 2018", W/ English Translation, 15 pgs.

"Chinese Application Serial No. 201580030239.6, Response Filed May 9, 2019 to Office Action dated Dec. 28, 2018", w/English Claims, 9 pgs.

"European Application Serial No. 15747589.8, Response filed Jul. 24, 2017 to Communication Pursuant to Rules 161(1) and 162 EPC dated Jan. 13, 2017", 14 pgs.

"Chinese Application Serial No. 201580030239.6, Decision of Rejection dated Sep. 4, 2019", W/ith English Translation, 10 pgs.

"Chinese Application Serial No. 201580030239.6, Request for Reexamination filed Dec. 19, 2019 to Decision of Rejection dated Sep. 4, 2019", w/ English claims, 20 pgs.

"European Application Serial No. 15747589.8, Response filed Apr. 12, 2021 to Communication Pursuant to Article 94(3) EPC dated Dec. 2, 2020", 13 pgs.

"European Application Serial No. 15747589.8, Communication Pursuant to Article 94(3) EPC dated Dec. 2, 2020", 6 pgs.

* cited by examiner

SYSTEMS AND METHODS FOR EVALUATING HEMODYNAMIC RESPONSE TO ATRIAL FIBRILLATION

CLAIM OF PRIORITY

This application claims the benefit of priority under 35 U.S.C. § 119(e) of U.S. Provisional Patent Application Ser. No. 62/006,595, filed on Jun. 2, 2014, which is herein incorporated by reference in its entirety.

TECHNICAL FIELD

This document relates generally to medical devices, and more particularly, to systems, devices and methods for assessing hemodynamic status during an atrial tachyarrhythmia such as atrial fibrillation.

BACKGROUND

Atrial fibrillation (AF) is the most common clinical arrhythmia, and accounts for approximately one third of admissions resulting from cardiac rhythm disturbances. An estimated 2.3 million people in North America have AF. During AF, the normal regular sinus rhythm is overwhelmed by disorganized electrical pulses originated from regions in or near an atrium. This can lead to irregular conductions to ventricles, thereby causing inappropriately fast and irregular heart rate. One type of AF is paroxysmal AF which may last from minutes to days before it stops by itself. Another type known as persistent AF may last for over a week and typically requires medication or other treatment to revert to normal sinus rhythm. The third type, permanent AF, is a condition where a normal heart rhythm cannot be restored with treatment. Persistent AF can become more frequent and result in permanent AF.

Congestive heart failure (CHF) is another major cardiovascular epidemic and affects over five million people in the United States alone. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood. CHF can affect the left heart, right heart or both sides of the heart, resulting in non-simultaneous contractions of the left ventricle and contractions of the right ventricle. Such non-simultaneous contractions, also known as dyssynchrony between the left and right ventricles, can further decrease the pumping efficiency of the heart.

There is a close pathophysiological relationship between AF and CHF. A large percentage of CHF patients may experience AF or other types of atrial tachyarrhythmias. AF may facilitate the development or progression of congestive heart failure (CHF), and CHF can increase the risk for the development of AF. The prevalence of AF in patients with CHF increased in parallel with the severity of CHF.

OVERVIEW

Atrial tachyarrrhthmias, such as AF, can coexist with heart failure (HF) in many CHF patients. AF may facilitate the development or progression of CHF in several ways. For example, during AF, irregularity of the ventricular contractions can result in reduction in left ventricular (LV) filling during short cycles which is not completely compensated for by increased filling during longer cycles. The loss of effective atrial contractile function also contributes to the deterioration of LV filling, particularly in CHF patients with diastolic dysfunction. Presence of untreated or uncontrolled AF may also reduce effectiveness of CHF therapies.

Timely and reliable detection of AF is necessary for treatment of AF and prevention of its exacerbating effect on CHF. Patients with AF frequently experience inappropriately rapid heart rate and irregular ventricular rhythm due to the loss of normal AV synchrony. The loss of normal AV synchrony and irregular ventricular rhythm can adversely impact the hemodynamic stability. For example, the loss of effective atrial contraction may reduce its contribution to ventricular filling, reduce the end-diastolic pressure and volume in the left and right ventricles, or increase the mean atrial diastolic pressure. AF may also result in shortened passive diastolic filling time, cause atrioventricular valvular regurgitation, thereby markedly decreasing cardiac output, especially for persons with impaired diastolic filling of the ventricles.

To prevent substantial hemodynamic deterioration, evaluation of the hemodynamic status can be critical for determining appropriate AF treatment or titrating AF therapies such as pharmacological or device therapies. On the other hand, the detrimental hemodynamic effects of AF can vary among patients. For example, an ongoing AF can cause more significant hemodynamic deterioration in patients with mitral stenosis, restrictive or hypertrophic cardiomyopathy, pericardial diseases, or ventricular hypertrophy. The present inventors have recognized that there remains a considerable need of systems and methods that can provide individualized evaluation of hemodynamic deterioration in patient experiencing AF.

Ambulatory medical devices (AMDs) can be used for monitoring HF patient and detecting HF worsening events. Examples of such ambulatory medical devices can include implantable medical devices (IMDs), subcutaneous medical devices, wearable medical devices or other external medical devices. The ambulatory or implantable medical devices can include physiologic sensors which can be configured to sense electrical activity and mechanical function of the heart, or physical or physiological variables associated with the signs and symptoms of worsening of HF. Some of these physiologic sensors can provide diagnostic features including information about the patient's hemodynamic status. For example, heart sounds are useful indicators of proper or improper functioning of a patient's heart, and can be used to assess a patient's hemodynamic status. Therefore, physiologic sensors such as heart sounds sensors can be used to assess adverse hemodynamic impact of the AF episode on a CHF patient. Various embodiments described in this document can help determine hemodynamic status during an AF episode.

Example 1 can include a system comprising an atrial tachyarrhythmia detection circuit to detect an atrial tachyarrhythmia including an AF episode, a hemodynamic sensor circuit to sense at least one hemodynamic signal, and a hemodynamic status analyzer circuit that can calculate one or more signal metrics using the sensed hemodynamic signal during the AF episode. The hemodynamic status analyzer circuit can categorize the hemodynamic status of the patient into one of two or more categorical hemodynamic status levels which indicate elevated hemodynamic impact caused by the detected AF episode. A user interface can provide to an end-user a presentation of the categorized hemodynamic status level during AF.

Example 2 can include, or can optionally be combined with the subject matter of Example 1 to optionally include a hemodynamic status analyzer circuit that can categorize the hemodynamic status of the patient into one of the two or more categorical hemodynamic status levels in response to the one or more signal metrics each meeting a respective criterion. In an example, the categorical hemodynamic levels include a hemodynamic stable status and a hemodynamic unstable status.

Example 3 can include, or can optionally be combined with the subject matter of one or any combination of Examples 1 and 2 to optionally include a user interface configured to provide a presentation of the categorized hemodynamic status level.

Example 4 can include, or can optionally be combined with the subject matter of one or any combination of Examples 1 through 3 to optionally include a hemodynamic status analyzer circuit that can calculate one or more signal metrics before the detection of the AF episode, and to categorize the hemodynamic status of the patient into one of the two or more categorical hemodynamic status levels using a comparison between the one or more signal metrics during the detected AF episode and the corresponding one or more signal metrics before the detection of the AF episode.

Example 5 can include, or can optionally be combined with the subject matter of one or any combination of Examples 1 through 4 to optionally include a heart sound sensor configured to sense a heart sound (HS) signal, and a heart sound component detector circuit configured to detect from the HS signal one or more HS components including an S1, an S2, an S3 or an S4 heart sound, wherein the hemodynamic status analyzer circuit can calculate one or more HS metrics indicative or correlative of hemodynamic status of the patient using the detected one or more HS components.

Example 6 can include, or can optionally be combined with the subject matter of Example 5 to optionally include a hemodynamic status analyzer circuit that can determine intensity of the one or more HS components, and a hemodynamic status analyzer circuit that can categorize the hemodynamic status of the patient into a categorical hemodynamic status level indicating a higher hemodynamic impact of the detected AF in response to a lower intensity of the one or more HS components.

Example 7 can include, or can optionally be combined with the subject matter of Example 6 to optionally include a cardiac activity sensor configured to sense a cardiac electrical activity including an atrial depolarization or a ventricular depolarization, and a hemodynamic status analyzer circuit that can determine the one or more HS metrics including a cardiac timing interval (CTI) using the sensed cardiac electrical activity and the detected one or more HS components.

Example 8 can include, or can optionally be combined with the subject matter of Example 7 to optionally include a hemodynamic parameter generator circuit that can determine a diastolic timing interval (DTI), and a hemodynamic status analyzer circuit that can categorize the hemodynamic status of the patient into a categorical hemodynamic status level indicating a higher hemodynamic impact of the detected AF in response to a shorter DTI.

Example 9 can include, or can optionally be combined with the subject matter Example 7 to optionally include a hemodynamic parameter generator circuit that can determine a variability of a diastolic timing interval (DTIvar), and a hemodynamic status analyzer circuit that can categorize the hemodynamic status of the patient into a categorical hemodynamic status level indicating a higher hemodynamic impact of the detected AF in response to a higher DTIvar.

Example 10 can include, or can optionally be combined with the subject matter of one or any combination of Examples 1 through 9 to optionally include an impedance sensor configured to sense an intrathoracic impedance signal, and a hemodynamic status analyzer circuit that can calculate one or more impedance metrics indicative or correlative of thoracic fluid status, and categorize the hemodynamic status of the patient into one of the two or more categorical hemodynamic status levels using at least the one or more impedance metrics.

Example 11 can include, or can optionally be combined with the subject matter of one or any combination of Examples 1 through 10 to optionally include a respiration sensor configured to sense a respiration signal, and a hemodynamic status analyzer that can calculate one or more respiration metrics indicative or correlative of respiration rate, respiration depth, or respiration pattern, and categorize the hemodynamic status of the patient into one of the two or more categorical hemodynamic status levels using at least the one or more respiration metrics.

Example 12 can include, or can optionally be combined with the subject matter of Examples 11 to optionally include a hemodynamic status analyzer circuit that can calculate a rapid shallow breathing index (RSBI), and to categorize the hemodynamic status of the patient into one of the two or more categorical hemodynamic status levels using at least the calculated RSBI.

Example 13 can include, or can optionally be combined with the subject matter of one or any combination of Examples 1 through 12 to optionally include a hemodynamic status analyzer circuit that can calculate a composite hemodynamic risk indicator (CRI) using the one or more signal metrics, and to categorize the hemodynamic status of the patient into one of the two or more categorical hemodynamic status levels using a comparison between the CRI and one or more threshold values.

Example 14 can include, or can optionally be combined with the subject matter of Example 13 to optionally include a hemodynamic status analyzer circuit that can calculate for each of the one or more signal metrics a respective individual hemodynamic risk score indicative of degree of hemodynamic compromise, and generate the CRI using a linear or nonlinear combination of the individual hemodynamic risk score of the one or more signal metrics.

Example 15 can include, or can optionally be combined with the subject matter of Example 13 to optionally include a hemodynamic status analyzer circuit that can generate the CRI using a probabilistic fusion of the one or more signal metrics.

Example 16 can include a method for assessing patient hemodynamic response to an AF episode. The method can include processes of detecting an AF episode, and receiving at least one hemodynamic signal obtained from a patient. The hemodynamic signal can include a heart sound signal, a thoracic impedance signal, or a respiration signal. One or more signal metrics can be generated using the sensed hemodynamic signal. The method includes using the signal metrics to categorize the patient's hemodynamic status into one of two or more categorical hemodynamic status levels that indicate elevated hemodynamic impact caused by the AF episode. A presentation of the categorized hemodynamic status level can be generated and presented to an end-user.

Example 17 can include, or can optionally be combined with the subject matter of Example 16 to optionally include classifying the hemodynamic status of the patient into either a hemodynamically stable status or a hemodynamically unstable status.

Example 18 can include, or can optionally be combined with the subject matter of one or any combination of Examples 16 and 17 to optionally include calculating one or more signal metrics before the detection of the AF episode, calculating a relative change of one or more signal metrics from before the detection of the AF episode to the corresponding one or more signal metrics during the detected AF episode, and categorizing the hemodynamic status of the patient into one of the two or more categorical hemodynamic status levels using the relative change of the one or more signal metrics.

Example 19 can include, or can optionally be combined with the subject matter of one or any combination of Examples 16 and 18 to optionally include receiving at least one hemodynamic signal includes receiving a heart sound (HS) signal, generating one or more signal metrics includes calculating intensity of one or more HS components including an intensity of an S1, an S2, an S3 or an S4 heart sound, and categorizing the hemodynamic status includes categorizing the hemodynamic status into a categorical hemodynamic status level indicating a higher hemodynamic impact of the detected AF in response to a lower intensity of the one or more HS components.

Example 20 can include, or can optionally be combined with the subject matter of one or any combination of Examples 16 and 18 to optionally include receiving at least one hemodynamic signal includes receiving a heart sound (HS) signal and a cardiac electrical activity, generating one or more signal metrics includes calculating a cardiac timing interval (CTI) using the sensed cardiac electrical activity and the detected one or more HS components, the CTI including a diastolic timing interval (DTI), and categorizing the hemodynamic status includes categorizing the hemodynamic status into a categorical hemodynamic status level indicating a higher hemodynamic impact of the detected AF in response to a shorter DTI.

Example 21 can include, or can optionally be combined with the subject matter of one or any combination of Examples 16 and 18 to optionally include receiving at least one hemodynamic signal includes receiving a heart sound (HS) signal and a cardiac electrical activity, generating one or more signal metrics includes calculating a variability of cardiac timing interval (CTIvar) using the sensed cardiac electrical activity and the detected one or more HS components, the CTIvar including a variability of diastolic timing interval (DTIvar), and categorizing the hemodynamic status includes categorizing the hemodynamic status into a categorical hemodynamic status level indicating a higher hemodynamic impact of the detected AF in response to a higher DTIvar.

Example 22 can include, or can optionally be combined with the subject matter of one or any combination of Examples 16 and 21 to optionally include calculating for each of the one or more signal metrics a respective individual hemodynamic risk score indicative of degree of hemodynamic compromise, generating a composite hemodynamic risk indicator (CRI) using a linear or nonlinear combination of the individual hemodynamic risk score of the one or more signal metrics, and categorizing the hemodynamic status of the patient into one of the two or more categorical hemodynamic status levels using a comparison between the CRI and one or more threshold values.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for assessing adverse hemodynamic impact of atrial tachyarrythmia such as an atrial fibrillation (AF) episode. By monitoring a patient's hemodynamic sensor response to one of a plurality of candidate AF therapies such as using a heart sound sensor, the systems and methods discussed in the present document can provide an end-user diagnostic with information including a categorized hemodynamic stability during AF. The systems and methods discussed in this document can also be used for evaluating hemodynamic effects of other atrial tachyarrhythmias such as atrial tachycardia or atrial flutter.

Figure 1:
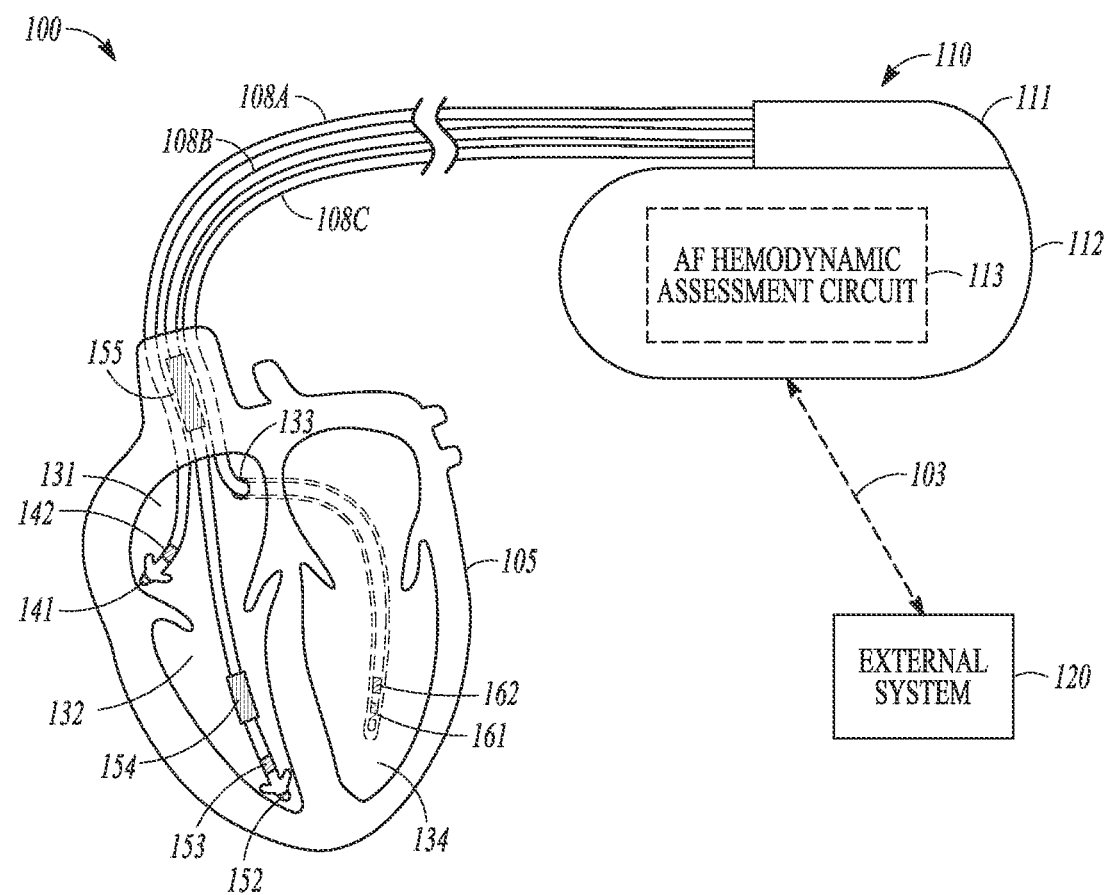
FIG. 1 illustrates an example of a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV. In some examples (not shown in FIG. 1), at least one of the leads 108A-C, or an additional lead other than the leads 108A-C, can be implanted under the skin surface without being within a heart chamber, or at or close to heart tissue.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include an AF hemodynamic assessment circuit 113. The AF hemodynamic assessment circuit 113 can be configured to detect an AF episode, sense a hemodynamic signal during the AF, and categorize the hemodynamic status into one of two or more categorical hemodynamic status levels indicative of elevated hemodynamic impact of the detected AF episode. A presentation containing the categorical hemodynamic status levels associated with the detected AF episode can be generated and provided to an end-user. Examples of the AF hemodynamic assessment circuit 113 are described below, such as with reference to FIGS. 2-5.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The AF hemodynamic assessment circuit 113 can be implemented at the external system 120 such as using data extracted from the IMD 110 or data stored in a memory within the external system 120. Portions of the AF hemodynamic assessment circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
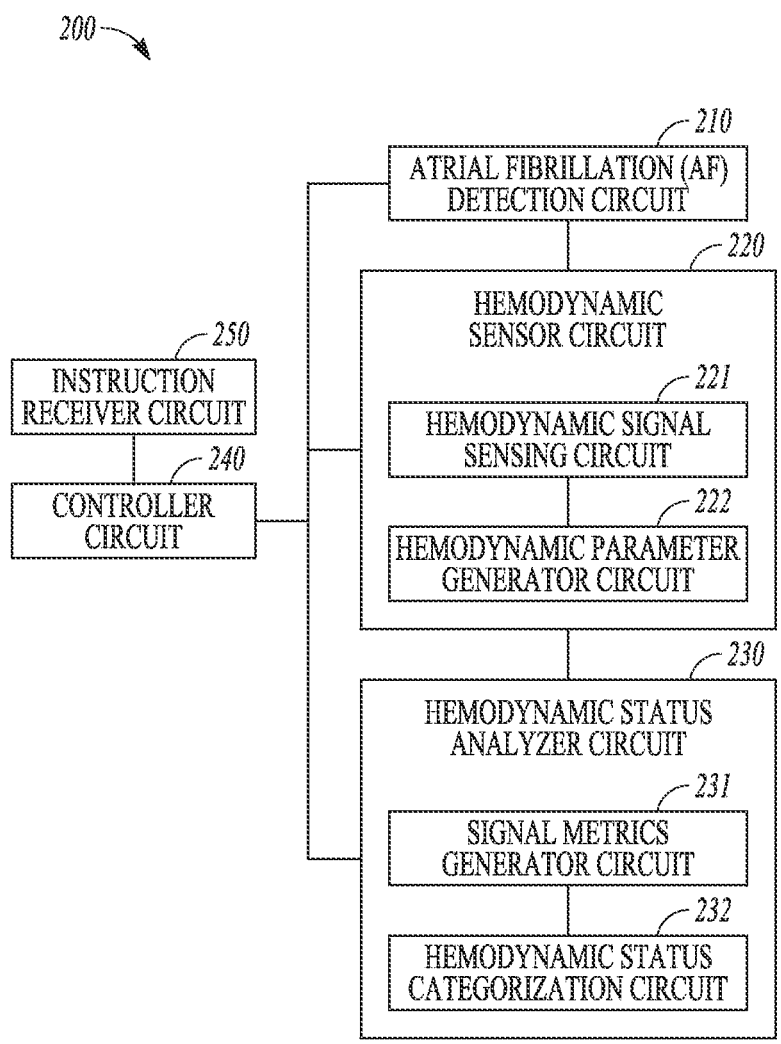
FIG. 2 illustrates an example of an AF hemodynamic assessment circuit.

FIG. 2 illustrates an example of an AF hemodynamic assessment circuit 200, which can be an embodiment of the AF hemodynamic assessment circuit 113. The AF hemodynamic assessment circuit 200 can include one or more of an AF detection circuit 210, a hemodynamic sensor circuit 220, a hemodynamic status analyzer circuit 230, a controller circuit 240, and an instruction receiver circuit 250.

The AF detection circuit 210 can be configured to detect an AF episode from a patient. The AF detection circuit 210 can be coupled to one or more physiologic sensors each configured to sense a physiologic signal indicative of presence of an AF episode. Examples of such physiologic signals can include electrocardiograms (ECGs) such as sensed by using electrodes non-invasively attached to the body surface, subcutaneous ECGs such as sensed by using subcutaneously placed electrodes, or intracardiac electrograms (EGMs) such as sensed by using electrodes on one or more of the leads 108A-C or the can 112. The physiologic signals can also include signals indicative of cardiac mechanical activities such as contractions of an atrium or a ventricle. The cardiac mechanical activities can include a signal sensed from an ambulatory accelerometer or a microphone configured to sense the heart sounds in a patient. The cardiac mechanical activities can include a signal sensed from an impedance sensor configured to sense intracardiac impedance change as a result of cyclic cardiac contractions. The AF detection circuit 210 can detect from the sensed physiologic signals atrial electrical events (such as P waves) or mechanical events, and ventricular electrical events (such as R waves or QRS complexes) or mechanical events, and detect an AF onset event when the atrial electrical or mechanical events or the ventricular electrical or mechanical events respectively meet a specified criterion. In an example, the AF detection circuit 210 can detect an AF onset event when the atrial rate exceeds a specified atrial rate threshold. In another example, the AF detection circuit 210 can detect an AF onset event when the ventricular rate exceeds a specified ventricular rate threshold and the variability of the ventricular rate exceeds a specified variability threshold.

The hemodynamic sensor circuit 220 can include a hemodynamic signal sensing circuit 221 and a hemodynamic parameter generator circuit 222. The hemodynamic signal sensing circuit 221 can be coupled, through wired or wireless link, to a hemodynamic sensor deployed outside or inside the patient's body, and can sense at least one hemodynamic signal indicative of hemodynamic status of the patient using the hemodynamic sensor. The hemodynamic sensor can include implantable, wearable, or other ambulatory physiologic sensors that directly or indirectly measure dynamics of the blood flow in a heart chamber or in a blood vessel. Examples of the hemodynamic sensors and the physiologic variables to sense can include a pressure sensor configured for sensing arterial pressure, pulmonary artery pressure, left atrial pressure, RV pressure, LV coronary pressure; impedance sensors configured for sensing thoracic impedance or cardiac impedance; a temperature sensor configured for sensing blood temperature; an accelerometer or a microphone configured for sensing one or more heart sounds; an optical sensor such as a pulse oximeter configured for sensing blood oxygen saturation; a chemical sensor configured for sensing central venous pH value.

The hemodynamic parameter generator circuit 222 can be configured to generate one or more hemodynamic parameters from the at least one sensed hemodynamic signal. The hemodynamic parameters can be characteristic features extracted or calculated from a hemodynamic signal. Examples of the hemodynamic parameters can include S1, S2, S3, or S4 heart sound components from the sensed heart sound signal, peak or trough impedance from the cardiac impedance signal, peak or trough blood pressure (corresponding respectively to systolic and diastolic pressures) from the blood pressure signal, or peak or trough of a respiration signal, or timing information associated with these signal components or characteristics.

The hemodynamic status analyzer circuit 230 can include a signal metrics generator circuit 231 and a hemodynamic status categorization circuit 232. The signal metrics generator circuit 231 can be configured to generate a plurality of measurements of the hemodynamic parameters such as measured at different time instants during a specified duration. The signal metrics can include a statistical index derived from the plurality of measurements of the hemodynamic parameters, such as mean, median or other central tendency measures, or second-order statistics including variance or standard deviation of the plurality of measurements, a histogram of the hemodynamic parameter intensity, or higher-order statistics calculated using the plurality of measurements. Alternatively or additionally, the signal metrics generator 231 can generate a signal metric using one or more signal trends of the hemodynamic parameter (such as intensity of the hemodynamic parameter over time), one or more signal morphological descriptors derived from the signal trend of the hemodynamic parameter, or signal power spectral density at a specified frequency range, among others.

The hemodynamic status categorization circuit 232 can be configured to categorize the hemodynamic status of the patient into one of two or more categorical hemodynamic status levels using the one or more signal metrics. The categorical hemodynamic status levels can indicate elevated adverse hemodynamic impact exerted by the AF episode on the patient. In an example, the two or more categorical hemodynamic status levels can be determined by comparing the one or more signal metrics to respective criteria, such as a plurality of threshold values. In another example, the categorical hemodynamic status levels include a "hemodynamically stable AF" category and a "hemodynamically unstable AF" category.

In an example, the hemodynamic sensor circuit 220 can sense a heart sound (HS) signal, and the hemodynamic status analyzer circuit 230 can calculate one or more HS signal metrics such as daily average S1, S2, or S3 heart sound intensity. Additionally or alternatively, the hemodynamic sensor circuit 220 can sense an impedance signal, such as an intrathoracic impedance signal (ITZ), using two or more electrodes on one or more leads 108A-C or the can 112. In an example, electric current can be injected across the electrode 154 and the can 112, resulting voltage can be sensed across the electrode 152 and the can 112, and the ITZ can be computed using the Ohm's law. The ITZ signal can be amplified, digitized, and filtered to a specified frequency range. In an example, the filtered ITZ can include the direct-current (DC) component of the impedance. The hemodynamic status analyzer circuit 230 can calculate a daily average of the filtered ITZ which can indicate or correlate to intrathoracic fluid accumulation status. In another example, the hemodynamic sensor circuit 220 can sense a respiration signal such as by using an impedance sensor, a thermocouple or thermistor-based air-flow sensor, or a piezo-resistive sensor, among others. The hemodynamic status analyzer circuit 230 can calculate one or more respiration metrics including a respiration rate, tidal volume or other indicators of respiration depth, or descriptors of respiration pattern such as apnea index indicating the frequency of sleep apnea, hypopnea index indicating the frequency of sleep hypopnea, apnea-hypopnea index (AHI) indicating the frequency of or sleep hypopnea events, or a rapid shallow breathing index (RSBI) computed as a ratio of respiratory frequency (number of breaths per minutes) to tidal volume. Examples of the HS-based hemodynamic sensor circuit 220 and the hemodynamic status analyzer circuit 230 are described below, such as with reference to FIGS. 3-5.

In some examples, the hemodynamic sensor circuit 220 can sense one or more hemodynamic signals and the hemodynamic status analyzer circuit 230 can categorize patient hemodynamic status only when a trigger signal is received. The trigger signal "wakes up" the processes of hemodynamic signal sensing and analysis. The trigger signal can be issued in response to a detection of an AF episode such as provided by the AF detection circuit 210, a certain time of day, or when patient is under a specified condition such as during sleep or awake, or when patient physical activity or exertion level is within a specified range. Alternatively, the trigger signal can be a command signal provided by an end-user such as via a user interface coupled to the instruction receiver circuit 250.

In some examples, the hemodynamic sensor circuit 220 can sense a baseline hemodynamic signal before the detection of the AF episode, and the hemodynamic status analyzer circuit 232 can perform analysis on the sensed baseline hemodynamic signal and calculate one or more baseline signal metrics. The hemodynamic status analyzer circuit 232 can categorize the hemodynamic status of the patient during a detected AF episode using a comparison of the one or more signal metrics during the detected AF episode and the corresponding one or more baseline signal metrics. For example, the hemodynamic status analyzer circuit 232 can categorize decrease in an intensity of a signal metric from its baseline value into one of a plurality of levels indicating various levels of hemodynamic deterioration resulted from the AF episode.

The controller circuit 240 can receive external programming input from the instruction receiver circuit 250 to control the operations of the AF detection circuit 210, the hemodynamic sensor circuit 220, the hemodynamic status analyzer circuit 230, and the data flow and instructions between these components. Examples of the instructions received by instruction receiver 250 can include parameters used in detecting an AF episode, sensing one or more of hemodynamic status signals, extracting hemodynamic parameters, generating signal metrics, and categorizing hemodynamic status into one of the two or more hemodynamic status levels. The instruction receiver circuit 250 can include a user interface configured to present programming options to the user and receive system user's programming input. In an example, at least a portion of the instruction receiver circuit 250, such as the user interface, can be implemented in the external system 120.

In an example, the AF hemodynamic assessment circuit 200 can additionally include, or be coupled to, a therapy delivery circuit configured to deliver AF therapy to the patient. The therapy delivery circuit can program one or more of therapy parameters or therapy types (such as cardiac pacing therapy, cardioversion therapy, or defibrillation therapy) based on the categorized hemodynamic status of the patient such as provided by the hemodynamic status categorization circuit 232. In an example, a more aggressive therapy, such as a defibrillation therapy, can be programmed and delivered to the patient if the categorized hemodynamic status indicates a more compromised hemodynamic status. A less aggressive therapy, such as a cardiac pacing therapy or a delayed defibrillation therapy, can be programmed and delivered if the categorized hemodynamic status indicates a less compromised hemodynamic status.

Figure 3:
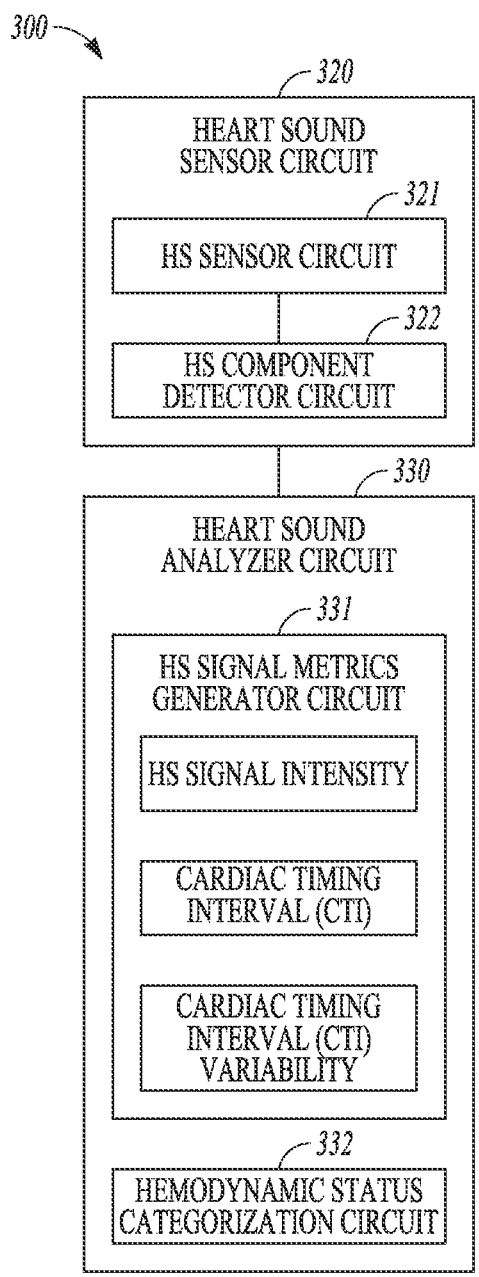
FIG. 3 illustrates an example of a heart sound (HS) sensing and analyzer circuit.

FIG. 3 illustrates an example of a heart sound (HS) sensing and analyzer circuit 300, which can comprises a heart sound sensors circuit 320 and a heart sound analyzer circuit 330. The HS sensing and analyzer circuit 300 can be configured to sense a HS signal generate one or more HS features indicative or correlative of hemodynamic status of the patient, and categorize the HS-based hemodynamic status into one of a plurality of hemodynamic status levels.

The heart sound sensor circuit 320 can be an embodiment of the hemodynamic sensor circuit 220. The HS sensor circuit 321 can be coupled to a heart sound sensor that can detect the heart sound or other forms of signals generated as a result of mechanical activities such as contraction and relaxation of a chamber of the heart. Examples of the HS sensors can include an ambulatory accelerometer or an ambulatory microphone. The heart sound sensor can be external to the patient or implanted inside the body. In an example, the heart sound sensor can be within an ambulatory medical device such as the IMD 110.

The HS component detector circuit 322 can process the sensed HS signal, including amplification, digitization, filtering, or other signal conditioning operations. In an example, the HS component detector circuit 322 can include one or more signal filters that can filter the sensed HS signal to a specified frequency range. For example, the HS component detector circuit 322 can include a bandpass filter adapted to filter the HS signal to a frequency range of approximately between 5 and 90 Hz. In another example, the HS component detector circuit 322 includes a bandpass filter adapted to filter the HS signal to a frequency range of approximately between 9 and 90 Hz. In an example, the HS component detector circuit 322 can include a double or higher-order differentiator configured to calculate a double or higher-order differentiation of the sensed heart sound signal.

The HS component detector circuit 322 can further detect, using the processed HS signal, one or more HS components including S1, S2, S3 or S4 heart sounds. In an example, the HS component detector circuit 322 can generate respective time windows for detecting one or more HS components. The time windows can be determined with reference to a physiologic event such as Q wave, R wave, or QRS complexes detected from a surface ECG, a subcutaneous ECG, or cardiac sensing events in an intracardiac EGM. For example, an S1 detection window can begin at 50 milliseconds (msec) following a detected R wave and have a duration of 300 msec. An S2 detection window can begin at specified offset following a detected R wave or S1 heart sound. An S3 detection window can be determined using at least one cardiac signal feature such as the R-wave timing or the timing of S2 heart sound. The S3 detection window can have a specified duration and can begin at a specified offset following the detected S2. In an example, the offset can be 125 msec, and the S3 window duration can be 125 msec. The offset or the S3 window duration can be a function of a physiologic variable such as a heart rate. For example, the offset can be inversely proportional to the heart rate, such that the S3 detection window can start at a smaller offset following the S2 at a higher heart rate.

The HS component detector circuit 322 can detect an HS component from at least a portion of the HS signal within the respective HS detection window. In an example, HS signal energy within a S2 detection window can be computed and compared to a S2 energy threshold, and an S2 component is detected in response to the HS signal energy exceeds the S2 energy threshold. In an example, the HS component detector circuit 322 can detect an HS component adaptively by tracking the temporal locations of the previously detected HS features. For example, an S3 heart sound can be detected by adaptively tracking the timing of historically detected S3 heart sounds. A dynamic programming algorithm can be used to detect and track the S3 heart sound within the S3 detection window, such as that disclosed in the commonly assigned Patangay et al. U.S. Pat. No. 7,853,327 entitled "HEART SOUND TRACKING SYSTEM AND METHOD," which is hereby incorporated by reference in its entirety.

The heart sound analyzer circuit 330 can be an embodiment of the hemodynamic status analyzer circuit 230, and include a HS signal metrics generator circuit 331 and a hemodynamic status categorization circuit 332. The HS signal metrics generator circuit 331 can generate one or more HS signal metrics using the HS components. As illustrated in FIG. 3, one example of the signal metric is HS intensity indicative of strength of a HS component, such as S1 intensity ($\|S1\|$), S2 intensity ($\|S2\|$), or S3 intensity ($\|S3\|$). During AF, deterioration of hemodynamic status can be reflected in a reduced HS intensity. Examples of the intensity of a HS component can include amplitude of a detected HS component in a time-domain HS signal, a transformed HS signal such as integrated HS energy signal, or in a frequency-domain HS signal such as the peak value of the power spectral density. In some examples, the HS signal metrics generator circuit 331 can measure the HS intensity as the peak value of a generic measurement within the respective HS detection window, such as peak envelop signal or root-mean-squared value of the portion of the HS signal within the HS detection window. Examples of HS intensity during a detected AF episode are described below, such as with reference to FIG. 4.

The HS signal metrics generator circuit 331 can alternatively or additionally calculate a signal metric of cardiac timing interval (CTI) using the sensed cardiac electrical activity and the detected HS component. The CTI represents the timing interval between two cardiac events such as a cardiac electrical event detected from the cardiac electrical signal and a mechanical event such as detected from a cardiac mechanical signal such as heart sound signal. The CTI can include a pre-ejection period (PEP), a systolic timing interval (STI), a diastolic timing interval (DTI), or a left ventricular ejection time (LVET), among others. The PEP represents the total duration of the electrical and mechanical events prior to ejection. The PEP can include the electrical-mechanical delay which occurs between the onset of the ventricular depolarization and the beginning of ventricular contraction, and the isovolumetric contraction time during which the left ventricle can contract prior to the opening of the aortic valve. The PEP can be measured using one or more physiologic signals. In an example, the PEP can be measured as the time duration from the onset of the QRS to the S1 heart sound, that is, PEP≈Q–S1 interval. The onset of the QRS can be determined from the ECG as the Q wave or the atrial activation event from the EGM such as the atrial EGM measured using one or more electrodes on the implantable lead 108A and the can 112. In another example, the PEP can be measured as the duration from the Q wave or the atrial activation event to the rise of the arterial pressure such as that measured from a carotid pulse wave. In an example, when no spontaneous QRS wave is present and the heart is electrically paced such as by using an IMD 110, the PEP can be measured from the ventricular pacing (Vp) signal to the beginning of ventricular ejection such as represented by the onset of S1 heart sound, that is, PEP≈Vp–S1 interval.

The STI represents the duration of total electro-mechanical systole. The STI spans from the electrical excitation of the heart to the closure of the aortic valve, and it contains two major components, namely the PEP and the LVET. The LVET represents the time interval from the opening to the closing of the aortic valve (mechanical systole). The STI can be measured using one or more physiologic signals sensed from physiologic sensors. Examples of the physiologic signals used for calculating STI or LVET include a heart sound signal, an intracardiac impedance signal, or a pressure signal. In an example, the STI can be measured as the interval from the onset of the QRS complex on the ECG or the atrial activation event in an intracardiac EGM to the S2 heart sound, that is, STI≈Q–S2 interval. In the case when the ventricle is paced (Vp), the STI can be measured from the ventricular pacing (Vp) signal to the end of ventricular ejection such as represented by the onset of S2 heart sound, that is, STI≈Vp–S2 interval.

The DTI represents the duration of total electro-mechanical diastole. The DTI spans from the closure of the aortic valve to the onset of the atrial depolarization in the next cardiac cycle. During AF, ventricular filing time can be reduced due to the fast atrial and ventricular contractions. A shortened DTI can result in deterioration of hemodynamic status. In an example, the DTI can be measured as the interval from the S2 heart sound to the onset of the QRS complex on the ECG or the atrial activation event in an intracardiac EGM of the next cardiac cycle, that is, DTI≈S2–Q interval. Therefore, a STI and the following DTI span the cardiac cycle, that is, CL=STI+DTI.

The CTI can also include composite measures using two or more of the STI, the DTI, the PEP, the cardiac cycle length (CL), or the LVET. Examples of the composite measures can include PEP/LVET ratio, STI/DTI ratio, STI/CL ratio, or DTI/CL ratio, among others. The irregular ventricular activity during AF can also lead increased variability of one or more of CTI measures. For example, the inappropriately irregular ventricular electrical excitation and mechanical contraction during AF can result in fluctuation in diastolic filing time, i.e., the DTI. The increased variability of DTI can further lead to widely varying stroke volume, thereby deteriorating patient's hemodynamic stability. As such, the variability of cardiac timing interval (CTIvar), such as the variability of STI, the variability of the DTI, or the variability of the PEP, can be indicative of the cardiac hemodynamics. The variability can be computed as a range, a variance, a standard deviation, or other measures of spreadness determined from a plurality of measurements of CTI.

The HS signal metrics generator circuit 331 can calculate the signal metrics of HS signal intensity, the CTI, or the CTI variability by generating a plurality of measurements of the corresponding parameters, and calculating a statistical index thereof, such as mean, median or other central tendency measures, or second-order statistics including variance or standard deviation of the measurements, a histogram of the hemodynamic parameter intensity, or higher-order statistics of the measurements. The hemodynamic status categorization circuit 230 can then categorize the HS signal intensity, the CTI, or the CTI variability into one of a plurality of levels of hemodynamic status that indicate elevated hemodynamic impact exerted by the AF episode on the patient. For example, the HS signal metrics generator circuit 331 can categorize the patient hemodynamic status into a categorical hemodynamic status level indicating a more significant hemodynamic impact of the detected AF in response to a lower intensity of the one or more HS components, a shorter DTI, or a higher DTI variability during the detected AF episode. Examples of hemodynamic status categorization circuit 300 are described below, such as with reference to FIG. 5.

Figure 4:
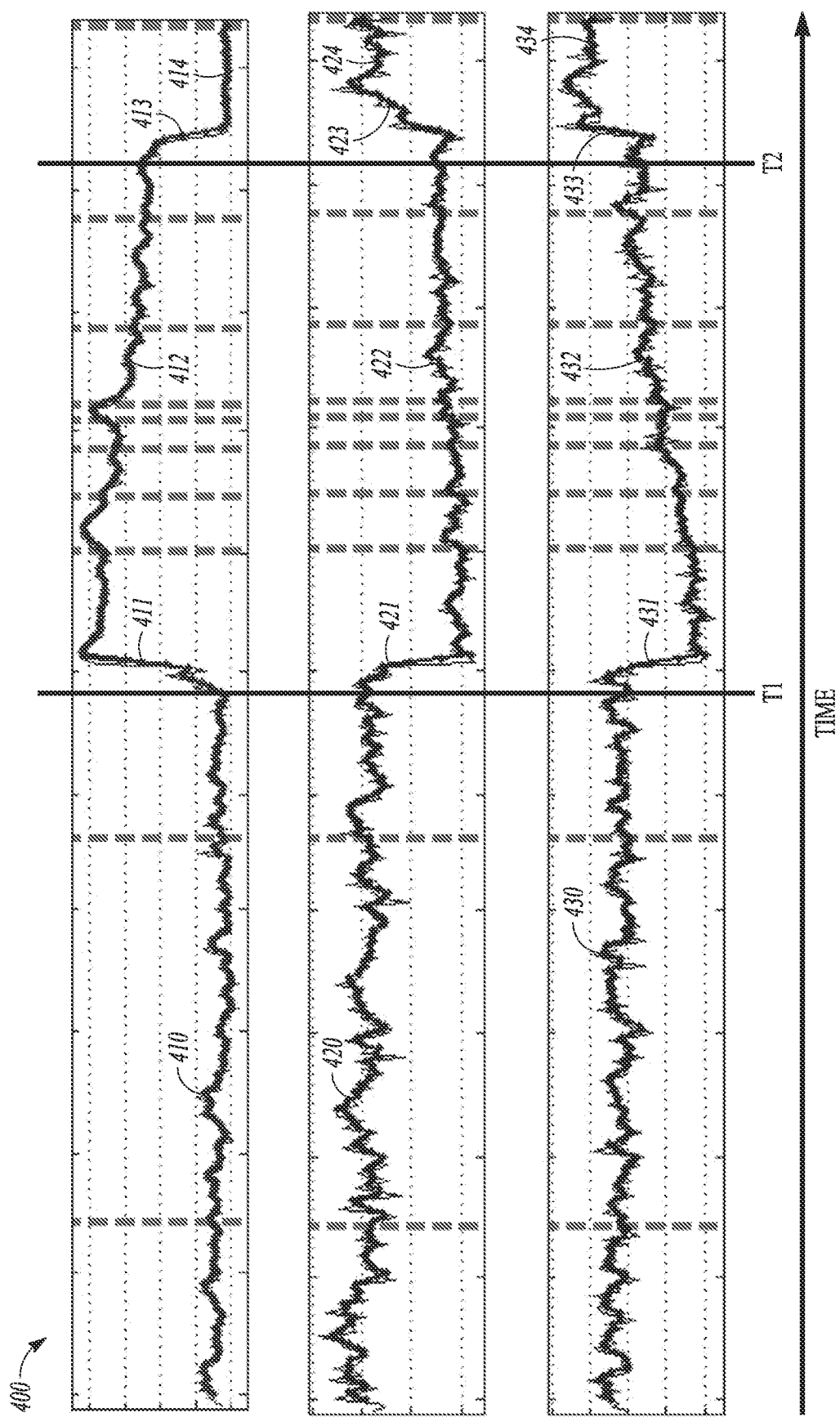
FIG. 4 illustrates an example of changes in heart rate (HR) and hemodynamic parameters during the onset and termination of an AF episode in a patient.

FIG. 4 illustrates an example 400 of changes in heart rate (HR) and hemodynamic parameters during the onset and termination of an AF episode in a patient. The daily average HR trend signal 410 represents temporal variation of the daily average HR signal over approximately 12 months. Drawn on the same time scale are a daily average S1 heart sound intensity (‖S1‖) trend signal 420 and a daily average S2 heart sound intensity (‖S2‖) trend signal 430. Signals 420 and 430 can be generated by the hemodynamic sensor circuit 220. The intensity of S1 and S2 are each computed as the signal power of S1 or S2 over respective time window.

As illustrated in FIG. 4, in response to an AF onset event occurring at time instant T1, the heart rate increases at 411, the ‖S1‖ decreases at 421 and the ‖S2‖ decreases at 431. During the sustained AF episode (between T1 and T2), the HR signal 412 remains at an elevated level and gradually decreases. Both the ‖S1‖ and ‖S2‖ signals remain lower than their respective pre-AF level, but gradually recover during the AF episode. At time instant T2, an AF termination event occurs. In response to the AF termination event, the heart rate decreases at 413, the ‖S1‖ increases at 423, and ‖S2‖ increases at 433. Following the transitional phases of AF termination, the HR signal 414, the ‖S1‖ signal 424, and the ‖S2‖ signal 434 reach or exceed their respective pre-AF level.

Figure 5:
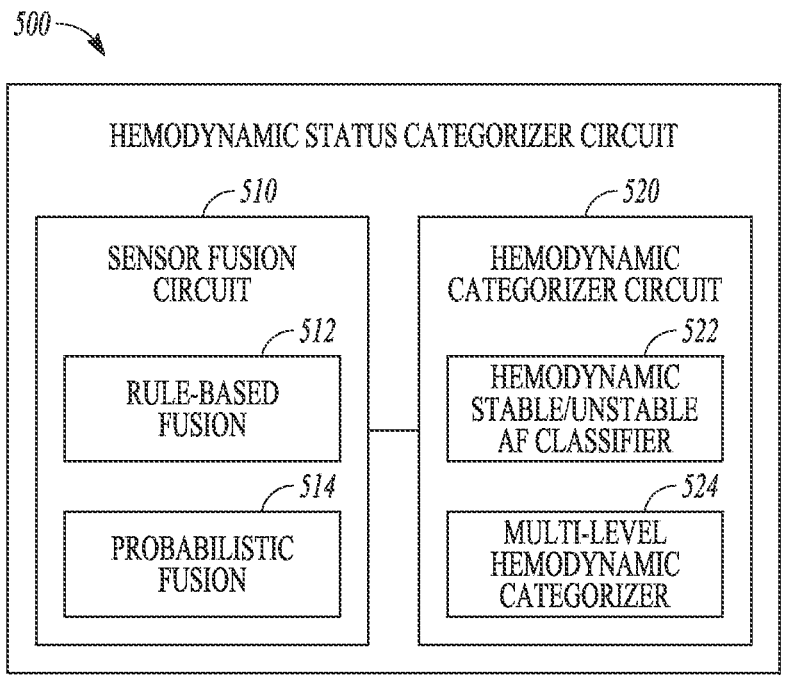
FIG. 5 illustrates an example of a multi-sensor hemodynamic status categorization circuit.

FIG. 5 illustrates an example of a multi-sensor hemodynamic status categorization circuit 500, which can be an embodiment of the hemodynamic status categorization circuit 232 or the hemodynamic status categorization circuit 332.

The hemodynamic status categorization circuit 500 can include a sensor fusion circuit 510 and a hemodynamic categorizer circuit 520. The sensor fusion circuit 510 can receive two or more signal metrics such as from the signal metrics generator circuit 231, and generate a composite risk index (CRI) indicating the significance of adverse hemodynamic impact of the AF episode. The two or more signal metrics can be generated using one or more hemodynamic signals, and can represent different physiologic characteristics or manifestations during an AF episode.

The sensor fusion circuit 510 can include one or both of a rule-based fusion 512 or a probabilistic fusion 514 of the two or more signal metrics. The rule-based fusion 512 can comprise a plurality of rules each defining a criterion for one or more of signal metrics, including S1 heart sound intensity (‖S1‖), S3 heart sound intensity (‖S3‖), respiration rate (RR), tidal volume (TV), rapid shallow breathing index (RSBI), or intrathoracic impedance (ITZ). The rule-based fusion 512 can comprise a combination of rules for hemodynamic deterioration, including an elevated RR, an elevated ‖S3‖, an elevated RSBI, a reduced ‖S1‖, a reduced ITZ, or a reduced TV. An individual hemodynamic risk score is assigned to a signal metric if it meets a specified criterion such as exceeding a specified threshold value. The CRI can be computed as a linear or nonlinear combination of the individual hemodynamic risk scores associated with the signal metrics used by the rule-based fusion 512.

In another example, a specified CRI can be pre-determined for a joint of two or more signal metrics each meeting their respective criterion. The mapping between the joint of signal metrics and the corresponding CRI can be constructed as a lookup table, an association map, or other forms of data structure, and stored in a memory. For example, during the AF episode, an X % reduction of ‖S1‖ and a Y % increase in RR from their respective baseline value can be mapped to a CRI score of 2. An X % reduction of ‖S1‖, a 5% increase in RR, and a Z % increase in ‖S3‖ can be mapped to a higher CRI score of 3. An X % reduction of ‖S1‖, a Y % increase in RR, a Z % increase in ‖S3‖, and a W % reduction of ITZ can be mapped to an even higher CRI score of 5. The mapping can be updated automatically or by an end-user based on the performance of the hemodynamic categorization. The update can also be adapted to changing patient context including patient health condition, activities or behaviors, progression of existing diseases, development of new diseases or conditions, or other patient clinical or non-clinical information.

As an alternative to the rule-based fusion 512, the probabilistic fusion 514 can include, for each of the one or more signal metrics, a descriptor of statistical distribution. Instead of assigning an empirical risk score as in the rule-based fusion 512, the probabilistic fusion 514 can determine the individual hemodynamic risk score or the CRI using the statistical distribution of the signal metrics and a probabilistic model, such as a Markov model, a hidden Markov model, a Bayesian network model, or a stochastic grammar model, among other stochastic graphical models. In an example, the probabilistic fusion 514 can use a Bayesian network model that encodes dependencies and causal relationships among the signal metrics and the hemodynamic status levels using probability measurements. The Bayesian networks can be constructed using prior knowledge including statistical distribution of signal metrics which can be estimated using data from a patient population. The probabilistic fusion 514 can determine a conditional probability of the patient having an AF episode with deteriorated hemodynamic stability given that the patient has pathophysiological manifestations such as the one or more signal metrics.

The hemodynamic categorizer circuit 520, coupled to the sensor fusion circuit 510, can determine a categorized hemodynamic status based on the CRI as provide by the sensor fusion circuit 510. The hemodynamic categorizer circuit can include one or both of the hemodynamic stable/unstable AF classifier 522, or a multi-level hemodynamic categorizer 524. The hemodynamic stable/unstable AF classifier 522 can classify the hemodynamic status as stable or unstable status based on a comparison between the CRI and a threshold value. The multi-level hemodynamic categorizer 524 can classify the hemodynamic status as one or three or more discrete levels of hemodynamic status by comparing the CRI to two or more different threshold values. In an example, the categorical hemodynamic levels can include "high hemodynamic deterioration", "medium hemodynamic deterioration", or "low hemodynamic deterioration."

Figure 6:
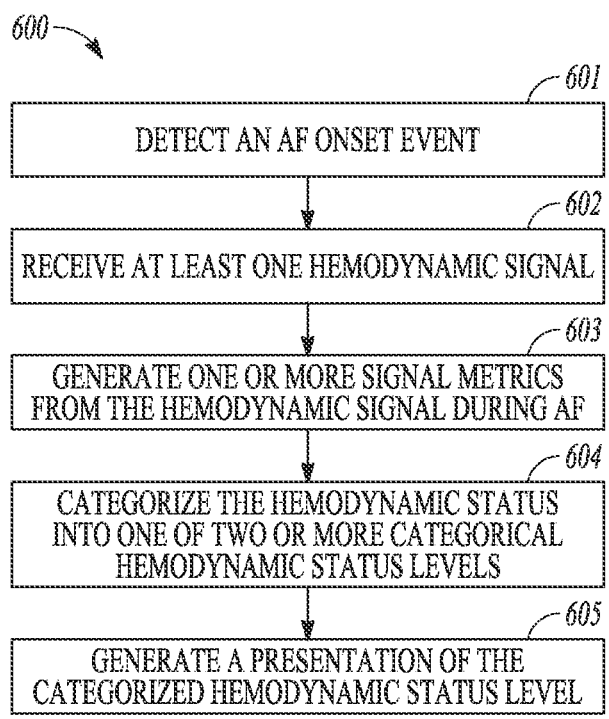
FIG. 6 illustrates an example of a method 600 for assessing hemodynamic status during an AF episode.

FIG. 6 illustrates an example of a method 600 for assessing hemodynamic status in a patient during atrial tachyarrhythmia such as an atrial fibrillation (AF) episode. The method 600 can be implemented and operate in an ambulatory medical device or in a remote patient management system. In an example, the method 600 can be performed by the AF hemodynamic assessment circuit 113 implemented in the IMD 110, or the external device 120 which can be in communication with the IMD 110.

At 601, an AF episode can be detected such as by using a system comprising the AF detection circuit 210. A physiologic signal can be sensed using one or more physiologic sensors. In an example, the AF episode can be detected using electrocardiograms (ECGs) such as sensed by using electrodes non-invasively attached to a patient's body surface, subcutaneous ECGs such as sensed by using subcutaneously placed electrodes, or intracardiac electrograms (EGMs) such as sensed by using electrodes on one or more of the leads 108A-C or the can 112. In an example, atrial rate can be determined from a ECG signal or an intracardiac EGM sensed at or near an atrium. An AF episode can be detected when the atrial rate exceeds a specified atrial rate threshold. In another example, ventricular rate and ventricular rate variability can be determined using the ECG signal or an intracardiac EGM sensed at or near a ventricle. An AF episode can be detected when the ventricular rate exceeds a specified ventricular rate threshold and the variability of the ventricular rate exceeds a specified variability threshold. Additionally or alternatively, a cardiac mechanical activity signal can be sensed using a physiologic signal such as pressure signal, impedance signal, or heart sound signal. A pulse rate and a variability of the pulse rate can be determined from the cardiac mechanical activity signal. An AF episode can be detected if the pulse rate exceeds a specified pulse rate threshold and the variability of the pulse rate exceeds a specified variability threshold.

At 602, at least one hemodynamic signal can be received during the detected AF, such as by using a hemodynamic sensor coupled to a sensing circuit such as the hemodynamic sensor circuit 220. The hemodynamic sensor can include implantable, wearable, or other ambulatory physiologic sensors that directly or indirectly measures dynamics of the blood flow in a heart chamber or in a blood vessel. Examples of the hemodynamic sensors and the physiologic variables to sense can include a pressure sensor configured for sensing arterial pressure, pulmonary artery pressure, left atrial pressure, RV pressure, LV coronary pressure; an impedance sensor configured for sensing thoracic impedance or cardiac impedance; a temperature sensor configured for sensing blood temperature; an accelerometer or a microphone configured for sensing one or more heart sounds; an optical sensor such as a pulse oximeter configured for sensing blood oxygen saturation; or a chemical sensor configured for sensing central venous pH value. From the received hemodynamic signal, one or more signal characteristics indicative or correlative of patient hemodynamics can be extracted.

At 603, one or more signal metrics can be generated from the at least one hemodynamic signal, such as by using a plurality of measurements of the hemodynamic parameters measured at different time instants during a specified duration. The signal metrics can include a statistical index such as mean, median or other central tendency measures, or second-order statistics including variance or standard deviation of the measurements, a histogram of the hemodynamic parameter intensity, or higher-order statistics of the measurements. The signal metric can also include one or more signal trends of the hemodynamic parameter (such as intensity of the hemodynamic parameter over time), one or more signal morphological descriptors derived from the signal trend of the hemodynamic parameter, or signal power spectral density at a specified frequency range.

At 604, the signal metrics can be used to categorize the patient's hemodynamic status into one of two or more categorical hemodynamic status levels. The categorical hemodynamic status levels can indicate escalated deterioration of the hemodynamic status caused by the AF episode. The categorical hemodynamic status levels can be determined by comparing the one or more signal metrics to a set of respective criteria, such as a plurality of threshold values. In an example, the categorical hemodynamic status levels include a "hemodynamically stable AF" category and a "hemodynamically unstable AF" category. Examples of using multiple signal metrics derived from different hemodynamic sensor signals for categorizing the hemodynamic status during AF are discussed below, such as with reference to FIG. 7.

At 605, a presentation of the categorized hemodynamic status can be generated and provided to an end-user such as via a user interface. The presentation can inform, warn, or alert a system end-user if a severe hemodynamic condition is detected. The presentation can include one or more media formats including, for example, a textual or graphical message, a sound, an image, or a combination thereof. In an example, the presentation can include recommended actions such as confirmative testing, diagnosis, or adjustment of therapy modalities or parameters.

Figure 7:
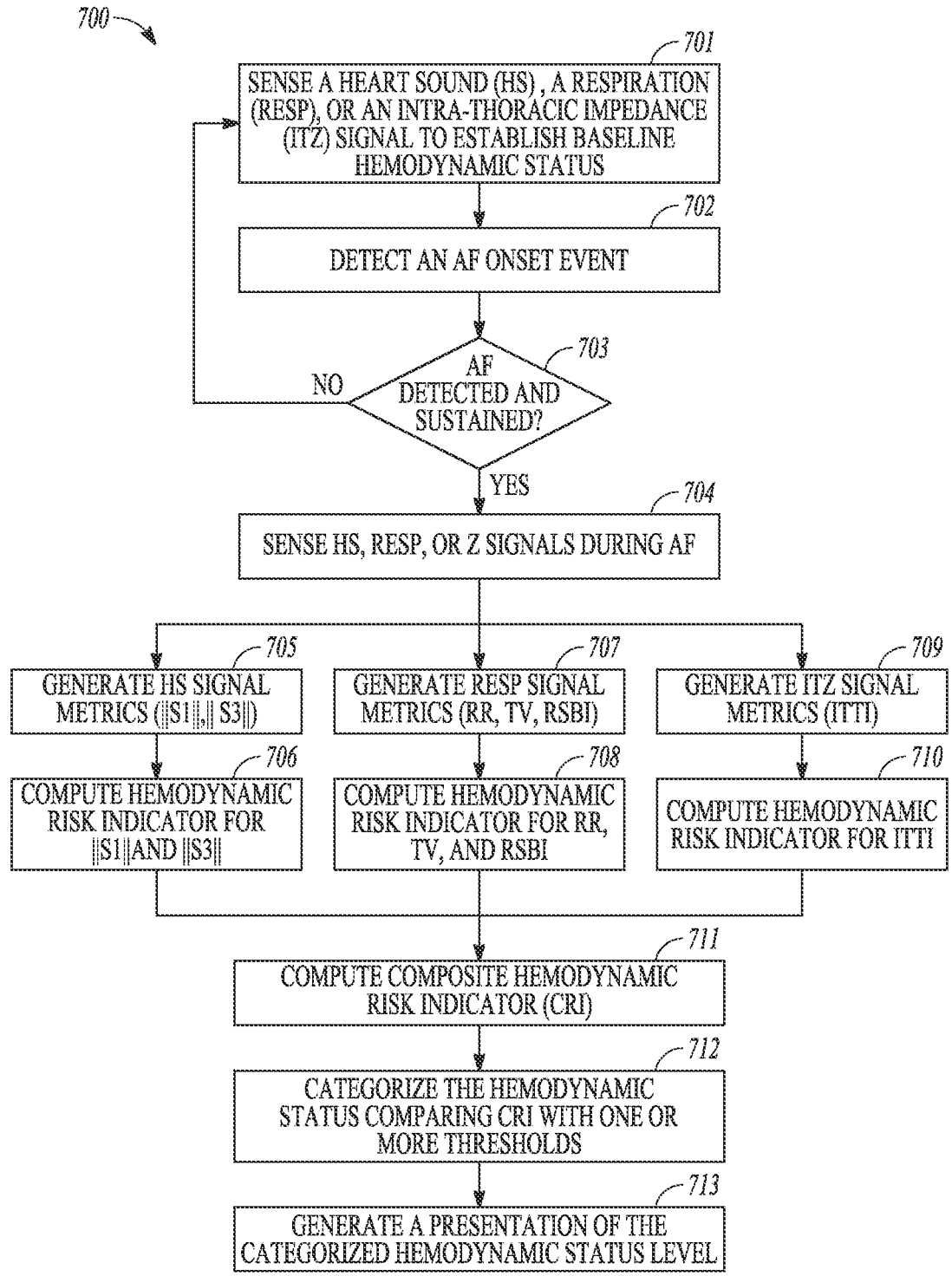
FIG. 7 illustrates an example of a method for assessing hemodynamic status during an AF episode using multiple hemodynamic signals

FIG. 7 illustrates an example of a method 700 for assessing hemodynamic status in a patient during AF using multiple hemodynamic signals. The method 700 can be an embodiment of the method 600. In an example, the method 700 can be performed by the AF hemodynamic assessment circuit 113.

The method 700 starts with a process of establishing baseline hemodynamic status using a plurality of hemodynamic signals including a heart sound (HS) signal, a respiration (RESP) signal, or an intrathoracic impedance (ITZ) signal. The HS signal can be sensed by using a heart sound sensor such as an ambulatory accelerometer or an ambulatory microphone. The RESP signal can be sensed using a thoracic impedance sensor, a thermocouple or thermistor-based air-flow sensor, or a piezo-resistive sensor, among others. The ITZ signal can be sensed using two or more electrodes on one or more leads 108A-C or the can 112. The sensed HS signal, RESP signal, or the ITZ signal can be respectively processed including amplification, digitization, filtering, or other signal conditioning operations. One or more signal characteristic can be extracted from the hemodynamic signals, including HS components such as an S1, an S2, an S3 or an S4 heart sounds extracted from the HS signal, peak or trough impedance from the ITZ signal, or peak or trough from the RESP signal.

At 702, an AF onset event can be detected. Similar to the process 601 of the method 600, the AF onset event detection can involve sensing a cardiac electrical signal such as an ECG or an intracardiac EGM, and detecting an AF onset event if the atrial rate exceeds a specified threshold, or if the ventricular rate and ventricular rate variability exceeds their respectively specified threshold. If at 703 no AF onset event is detected or the AF episode does not sustain for a specified minimal duration, then the hemodynamic signals monitoring and baseline hemodynamic status evaluation can be continued at 701. If an AF onset event is detected and sustains for a specified minimal duration, the hemodynamic signals, including the HS signal, RESP signal, or the ITZ signal, can be measured during the AF episode at 704.

One or more signal metrics can be generated from respective hemodynamic signals. For example, at 705, one or more HS signal metrics can be generated using at least the HS components. In one example, the HS signal metric includes intensity of a HS component, such as S1 intensity ($\|S1\|$), S2 intensity ($\|S2\|$), or S3 intensity ($\|S3\|$). Reduction of HS component intensity during AF can be indicative of deterioration of hemodynamic status. The intensity of an HS component can be computed as an amplitude of a detected HS component in a time-domain HS signal, a transformed HS signal such as integrated HS energy signal, a peak value of the power spectral density in a frequency-domain HS signal, or a peak value of a generic measurement within the respective HS detection window, such as peak envelop signal or root-mean-squared value of the portion of the HS signal within the HS detection window. In another example, the HS signal metric can include a cardiac timing interval (CTI) using the sensed cardiac electrical activity and the detected HS component. The CTI represents the timing interval between two cardiac events such as a cardiac electrical event detected from the cardiac electrical signal and a mechanical event such as detected from a cardiac mechanical signal or a hemodynamic signal such as heart sound signal. The CTI can include a systolic timing interval (STI), a diastolic timing interval (DTI), or a pre-ejection period (PEP), among others. The CTI can also include composite measures among STI, DTI, PEP, cardiac cycle (CL), or left ventricular ejection time (LVET). Examples of the composite measures can include PEP/LVET ratio, STI/DTI ratio, STI/CL ratio, or DTI/CL ratio, among others. In yet another example, the HS signal metric can include a variability of one or more of CTI measures. The variability can be computed as a range, a variance, a standard deviation, or other measures of spreadness determined from a plurality of measurements of CTI.

An individual hemodynamic risk score associated with the HS signal metrics can be determined at 706. A predetermined individual hemodynamic risk score can be determined if the HS signal metric meets a specified criterion such as exceeding a specified threshold value. In an example, a relative change of S1 heart sound intensity ($\|S1\|$) or S3 heart sound ($\|S3\|$) from the respective baseline level determined at 701 can each indicate hemodynamic status during AF. If $\|S1\|$ substantially decreases from its baseline level by at least a threshold value, or if $\|S3\|$ substantially increases from its baseline level by at least a threshold value, then a higher individual hemodynamic risk score can be assigned at 706, indicating more significant adverse hemodynamic impact caused by the AF episode. Conversely, if $\|S1\|$ does not substantially decrease from its baseline or if $\|S3\|$ does not substantially increase from its baseline level, then a lower individual hemodynamic risk score can be assigned at 706.

Similar to HS signal metrics generation process at 705, one or more RESP signal metrics can be generated at 707, or one or more ITZ signal metrics can be generated at 709. The RESP signal metrics can include respiration rate (RR), tidal volume (TV) or other indicators of respiration depth, or a descriptor of respiration pattern, such as apea index indicating the frequency of sleep apnea, hypopnea index indicating the frequency of sleep hypopnea, apnea-hypopnea index (AHI) indicating the frequency of or sleep hypopnea events, or a rapid shallow breathing index (RSBI) computed as a ratio of respiratory frequency (number of breaths per minutes) to tidal volume. The ITZ metrics can include daily average intrathoracic total impedance (ITTI) that contains a direct-current (DC) component of a wide-band ITZ signal. The daily average ITTI can be indicative or correlative of thoracic fluid accumulation status of the patient. A substantial decrease in ITTI during a sustained AF can be indicative of excessive fluid accumulation in a patient's chest, which may significantly deteriorate the patient's hemodynamic status.

Similar to the determination of the individual hemodynamic risk score for HS signal metrics such as $\|S1\|$ or $\|S3\|$ at 706, an individual hemodynamic risk score associated with the RESP signal metrics such as RR, TV, or RSBI can be determined at 708, and an individual hemodynamic risk score associated with the ITZ signal metrics such as daily average ITTI can be determined at 710. In an example, a relative change of RR, TV, or RSBI from their respective baseline level (such as determined at 701) can each indicate hemodynamic status during AF. If TV substantially decreases from its baseline level by at least a threshold value, or if RR or RSBI substantially increases from their respective baseline level by at least a respective threshold value, then a higher individual hemodynamic risk score can be assigned at 708, indicating more significant adverse hemodynamic impact caused by the AF episode. Conversely, if TV does not substantially decrease from its baseline, or if RR or RSBI does not substantially increase from their respective baseline level, then a lower individual hemodynamic risk score can be assigned at 708. Similarly, if ITTI substantially decreases from its baseline level by at least a threshold value, then a higher individual hemodynamic risk score can be assigned at 710, indicating more significant adverse hemodynamic impact caused by the AF episode. If ITTI does not substantially decrease from its baseline, then a lower individual hemodynamic risk score can be assigned at 710.

At 711, a composite hemodynamic risk indicator (CRI) can be computed using the individual hemodynamic risk scores for various signal metrics, such as those provided by 706, 708, or 710. The CRI can indicate the significance of adverse hemodynamic impact of the AF episode on the patient. In an example, the CRI can be computed as a linear or nonlinear combination of the individual hemodynamic risk scores associated with the signal metrics. In another example, the CRI can be computed using at least respective statistical distributions of the signal metrics and a probabilistic model, such as a Markov model, a hidden Markov model, a Bayesian network model, or a stochastic grammar model, among other stochastic graphical models. In an example, the CRI can be computed using a Bayesian network model that encodes dependencies and causal relationships among the signal metrics and the hemodynamic status levels using probability measurements. The Bayesian networks can be constructed using prior knowledge including statistical distribution of signal metrics which can be estimated using data from a patient population. The CRI can be a conditional probability of the patient having an AF with deteriorated hemodynamic stability given that the patient has pathophysiological manifestations such as the one or more signal metrics. In another example, a specified CRI can be pre-determined for a joint of two or more signal metrics each meeting their respective criterion. The mapping between the joint of signal metrics and the corresponding CRI can be constructed as a lookup table, an association map, or in other forms of data structure, and stored in a memory.

At 712, the patient hemodynamic status can be categorized using the CRI value. In an example, the CRI can be compared against a specified hemodynamic threshold value to classify the patient hemodynamic status as being either a hemodynamic stable AF or a hemodynamically unstable AF class. In another example, the CRI can be compared against multiple different threshold values or value ranges to classify the patient hemodynamic status into one of multiple classes such as "high hemodynamic deterioration", "medium hemodynamic deterioration", or "low hemodynamic deterioration." A presentation of the categorized hemodynamic status can be generated and provided to the end-user at 713.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A medical system, comprising:
   an atrial tachyarrhythmia detection circuit configured to detect a first atrial fibrillation (AF) episode in a patient over a first period and a second AF episode in the patient over a second period;
   a hemodynamic status analyzer circuit configured to:
      receive heart sound (HS) information of the patient during the first and second detected AF episodes and calculate one or more HS metrics using the received HS information during the first and second detected AF episodes;
      determine a first categorical hemodynamic status level for the first detected AF episode, and a second categorical hemodynamic status level for the second detected AF episode, using the one or more HS metrics calculated respectively from the HS information received during the first and second AF episodes, the first and second categorical hemodynamic status levels each indicative of a discrete level of patient hemodynamic stability; and determine a first candidate AF therapy to treat the first AF episode based on the first categorical hemodynamic status level, and a second candidate AF therapy, different from the first candidate AF therapy, to treat the second AF episode based on the second categorical hemodynamic status level, wherein to determine the first and second categorical hemodynamic status levels, the hemodynamic status analyzer circuit is configured to generate a composite hemodynamic risk indicator (CRI) using the calculated one or more HS metrics, and to determine the first and second categorical hemodynamic status levels using a comparison between the CRI and one or more threshold values; and an output unit configured to provide a presentation of the CRI to a user or a process to effect a treatment.

2. The system of claim 1, wherein the hemodynamic status analyzer circuit is configured to calculate one or more HS metrics before the detection of the first and second AF episodes, and to determine the first and second categorical hemodynamic status levels respectively for the first and second detected AF episodes using a comparison between the one or more HS metrics during the first and second detected AF episodes and the corresponding one or more HS metrics before the detection of the first and second AF episodes.

3. The system of claim 1, wherein the hemodynamic status analyzer circuit is configured to receive cardiac electrical activity of the patient including an atrial depolarization or a ventricular depolarization and to determine the one or more HS metrics including a cardiac timing interval (CTI) using the cardiac electrical activity and the one or more HS metrics.

4. The system of claim 3, wherein the hemodynamic status analyzer circuit is configured to determine the CTI including a diastolic timing interval (DTI), and to determine the first or the second categorical hemodynamic status level indicating a higher hemodynamic impact of the detected AF in response to the DTI being below a threshold.

5. The system of claim 3, wherein the hemodynamic status analyzer circuit is configured to determine a measure of variability of CTI including a variability of a diastolic timing interval (DTIvar), and to determine the first or the second categorical hemodynamic status level indicating a higher hemodynamic impact of the detected AF in response to the DTIvar being above a threshold.

6. The system of claim 1, including a hemodynamic sensor circuit configured to sense a HS signal indicative of a hemodynamic status of the patient, wherein the hemodynamic sensor circuit includes an impedance sensor configured to sense an intrathoracic impedance signal, wherein the hemodynamic status analyzer circuit is configured to calculate one or more impedance metrics indicative or correlative of thoracic fluid status and to determine the first and second categorical hemodynamic status levels using at least the one or more impedance metrics.

7. The system of claim 1, including a hemodynamic sensor circuit configured to sense a HS signal indicative of a hemodynamic status of the patient, wherein the hemodynamic sensor circuit includes a respiration sensor configured to sense a respiration signal, wherein the hemodynamic status analyzer circuit is configured to calculate one or more respiration metrics indicative or correlative of respiration rate, respiration depth, or respiration pattern and to determine the first and second categorical hemodynamic status levels using at least the one or more respiration metrics.

8. The system of claim 1, comprising a therapy circuit configured to determine or adjust an AF therapy for delivery to the patient, wherein:

the hemodynamic status analyzer circuit is configured to determine a hemodynamic impact of the AF therapy using a HS signal sensed in response to the AF therapy delivered to the patient; and the therapy circuit is configured to adjust the AF therapy using the determined hemodynamic impact of the detected first or second AF episode.

9. The system of claim 1, wherein the one or more HS metrics include at least one of a first heart sound component (S1) intensity or a second heart sound component (S2) intensity, and wherein the hemodynamic status analyzer circuit is configured to determine the first or the second categorical hemodynamic status level indicating a higher hemodynamic impact of the detected AF episode in response to a decrease in S1 intensity or a decrease in S2 intensity over time.

10. The system of claim 1, wherein the one or more HS metrics include a first heart sound component (S1) intensity and a second heart sound component (S2) intensity, and wherein the hemodynamic status analyzer circuit is configured to determine the first or the second categorical hemodynamic status level indicating a higher hemodynamic impact of the detected AF episode in response to a decrease in S1 intensity and a decrease in S2 intensity over time.

11. A method of operating a medical system, the method comprising:

detecting, using an atrial tachyarrhythmia detection circuit, a first atrial fibrillation (AF) episode in a patient over a first period and a second AF episode in the patient over a second period;

receiving, using a hemodynamic status analyzer circuit, heart sound (HS) information of the patient during the first and second detected AF episodes;

calculating one or more HS metrics using the received HS information during the first and second AF episodes;

determining, using the hemodynamic status analyzer circuit, a first categorical hemodynamic status level for the first detected AF episode, and a second categorical hemodynamic status level for the second detected AF episode using the one or more HS metrics calculated respectively from the HS information received during the first and second AF episodes, wherein determining the first and second categorical hemodynamic status levels includes:

calculating for each of the first and second HS metrics a respective individual hemodynamic risk score indicative of degree of hemodynamic compromise for each of the first and second detected AF episodes;

generating a composite hemodynamic risk indicator (CRI) for each of the first and second detected AF episodes using a linear or nonlinear combination of the individual hemodynamic risk score of the first and second HS metrics; and determining the first and the second categorical hemodynamic status levels using a comparison between the CRI and one or more threshold values;

determining, using the hemodynamic status analyzer circuit, a first candidate AF therapy to treat the first AF episode based on the first categorical hemodynamic status level, and a second candidate AF therapy, different from the first candidate AF therapy, to treat the second AF episode based on the second categorical hemodynamic status level; and providing, via an output unit, a presentation of the CRI to a user or a process to effect a treatment.

12. The method of claim 11, comprising:

calculating one or more HS metrics before detecting the first and second AF episodes;

calculating a relative change of one or more HS metrics from before detecting the first and second AF episodes to the corresponding one or more HS metrics during the detected first and second AF episodes; and determining the first and second categorical hemodynamic status levels respectively for the first and second detected AF episodes using the relative change of the one or more HS metrics.

13. The method of claim 11, comprising calculating intensity of one or more HS components using the received HS information; and wherein determining the first and second categorical hemodynamic status levels includes using a change in intensity of the one or more HS components over time.

14. The method of claim 11, wherein receiving the HS information includes receiving a heart sound (HS) signal and cardiac electrical activity, and wherein determining the first and second categorical hemodynamic status levels includes:

calculating a cardiac timing interval (CTI) using the cardiac electrical activity and one or more HS components of the HS signal, the CTI including a diastolic timing interval (DTI); and determining the first or the second categorical hemodynamic status level indicating a higher hemodynamic impact of the detected AF in response to a shorter DTI.

15. The method of claim 11, wherein receiving the HS information includes receiving a heart sound (HS) signal and cardiac electrical activity, and wherein determining the first and second categorical hemodynamic status levels includes:

calculating a variability of cardiac timing interval (CTIvar) using the cardiac electrical activity and one or more HS components of the HS signal, the CTIvar including a variability of diastolic timing interval (DTIvar); and determining the first or the second categorical hemodynamic status level indicating a higher hemodynamic impact of the detected AF in response to a higher DTIvar.

16. A medical system, comprising:

an atrial tachyarrhythmia detection circuit configured to detect a first atrial fibrillation (AF) episode in a patient over a first period and a second AF episode in the patient over a second period;

a hemodynamic status analyzer circuit configured to:

receive heart sound (HS) information of the patient during the first and second detected AF episodes;

for each of the first and second AF episodes, determine a first heart sound (S1) intensity and a second heart sound (S2) intensity using the received HS information corresponding to the respective AF episode;

determine first and second categorical hemodynamic status levels for the respective first and second AF episodes using one or more of the S1 intensity or the S2 intensity corresponding to the respective first and second AF episodes; and determine a first candidate AF therapy to treat the first AF episode based on the first categorical hemodynamic status level, and a second candidate AF therapy, different from the first candidate AF therapy, to treat the second AF episode based on the second categorical hemodynamic status level, wherein to determine the first and second categorical hemodynamic status levels, the hemodynamic status analyzer circuit is configured to generate a composite hemodynamic risk indicator (CRI) using one or more of the S1 intensity or the S2 intensity, and to determine the first and second categorical hemodynamic status levels using a comparison between the CRI and one or more threshold values; and an output unit configured to provide a presentation of the CRI to a user or a process to effect a treatment.

17. The system of claim 16, comprising a therapy circuit configured to deliver or adjust the AF therapy based on the determined categorical hemodynamic status level for the detected first or second AF episode.

* * * * *